United States Patent [19]

Neri et al.

[11] 3,962,250

[45] June 8, 1976

[54] OXIDATION PRODUCTS OF COBALT COMPLEXES, PROCESS FOR OBTAINING SAME AND INSERTION PROCESS

[75] Inventors: Carlo Neri; Emilio Perrotti, both of San Donato Milanese, Italy

[73] Assignee: Snam Progetti S.p.A., Milan, Italy

[22] Filed: Apr. 8, 1974

[21] Appl. No.: 459,125

Related U.S. Application Data

[62] Division of Ser. No. 102,977, Dec. 30, 1970, Pat. No. 3,803,192.

[30] Foreign Application Priority Data

Dec. 30, 1969  Italy.................................. 26424/69

[52] U.S. Cl........................ 260/270 D; 260/439 R; 260/270 PY
[51] Int. Cl.² ................ C07F 00/00; C07D 213/02; C07D 215/02
[58] Field of Search....... 260/439 R, 270 D, 270 PY

[56] References Cited
UNITED STATES PATENTS

| | | | |
|---|---|---|---|
| 3,562,307 | 2/1971 | Costa et al. | 260/439 R |
| 3,562,308 | 2/1971 | Costa et al. | 260/439 R |
| 3,567,751 | 3/1971 | Costa et al. | 260/439 R |
| 3,584,021 | 6/1971 | Costa et al. | 260/439 R |
| 3,584,022 | 6/1971 | Costa et al. | 260/439 R |
| 3,590,062 | 6/1971 | Casta et al. | 260/439 R |
| 3,636,007 | 1/1972 | Calderazzo | 260/439 R |
| 3,787,464 | 1/1974 | Neri et al. | 260/439 R |
| 3,803,192 | 4/1974 | Neri et al. | 260/439 R |
| 3,809,632 | 5/1974 | Costa et al. | 260/439 R |

FOREIGN PATENTS OR APPLICATIONS

1,196,776  7/1970  United Kingdom............. 260/439 R

OTHER PUBLICATIONS

Bailes et al., J.A.C.S., vol. 69, pp. 1886–1893 (1947).
Costa et al., J. Organometal 15, (1968), p. 189.
Harle et al., J.A.C.S., vol. 68, pp. 2612–2618 (1946).
Calvin et al., J.A.C.S., vol. 68, pp. 2254–2256 (1946).

*Primary Examiner*—Helen M. S. Sneed
*Attorney, Agent, or Firm*—Ralph M. Watson

[57] ABSTRACT

Processes are disclosed for preparing trivalent cobalt complexes having the formulas $$[Co^{III}(L_1L_2L_3L_4)]_2 \ CR_1CR_2O \cdot 2CR_1R_2OH \qquad (1)$$

and $$[Co^{III}(L_1L_2L_3L_4)] \ CR_1R_2O \cdot CR_1R_2OH \cdot B \qquad (2)$$

wherein $(L_1L_2L_3L_4)$ is a planar tetradentate ligand selected from bis-(diacetylmonoximeimino)-propane, bis-(salicylaldehyde)-ethylenediamine and bis-(acetylacetone)-ethylenediamine; $CR_1R_2O$ is an alcohol radical selected from $CH_3O$, $ClCH_2CH_2O$, $\phi CH_2O$ and $CH_2=CH-CH_2O$; $CR_1R_2OH$ is the corresponding alcohol; and B is an amine base by reacting cobalt complex $Co(L_1L_2L_3L_4)$, alcohol $CR_1R_2OH$ and amine base B with molecular oxygen at a temperature from 0° to 70°C.

3 Claims, No Drawings

OXIDATION PRODUCTS OF COBALT COMPLEXES, PROCESS FOR OBTAINING SAME AND INSERTION PROCESS

This is a division of application Ser. No. 102,977, filed December 30, 1970 now U.S. Pat. No. 3,803,192.

The present invention refers to new cobalt compounds and to the process for obtaining same.

More particularly, the present invention refers to a process for the preparation of cobalt oxidation products.

It is known there are divalent cobalt complexes having the following formula:

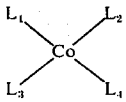

wherein $L_1$, $L_2$, $L_3$ and $L_4$ may belong to the same ligand molecule, for example a planar tetradentate ligand as bis-(diacetylmonoximeimino)-propane, bis-(salicylaldehyde)-ethylenediamine, or bis-(acetylacetone)-ethylenediamine; or may belong to two molecules of a bidentate ligand which may be selected from o-phenantroline, 2-2' dipyridil, nitroketons, acetylacetone, orthonitrosophenol, bidentate Schiff bases having the formula

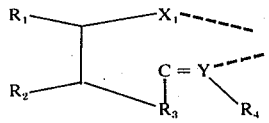

in which $R_1$, $R_2$, $R_3$ and $R_4$ may be hydrogen, substituted and unsubstituted alkyl or aryl radicals, $X_1$ may be oxygen, sulphur or nitrogen, whereas Y always is nitrogen, or they may be four monodentate ligands, equal or different, as nitriles, amines, phosphines, thioalcohols, nitrocompounds, halogen ions and so on.

It has now been found, that is an object of the present invention, the above cobalt complexes may be oxidized by molecular oxygen in presence of alcohols as methyl alcohol, ethylene, chlorohydrin, ethylene glycol, benzyl alcohol, allyl alcohol and the like.

The oxidation reaction is carried out in a homogeneous or heterogeneous phase of the corresponding alcohol.

Oxygen is allowed to bubble at a temperature ranging from 0° to 70° C and preferably at room temperature and at a pressure equal to or slightly higher than atmospheric.

According to the process of the present invention, the oxidation reaction may be carried out in the presence of both an anhydrous alcohol and an aqueous alcohol; moreover, it is possible to employ both the alcohol by itself and the alcohol mixed with inert diluents as aliphatic or aromatic hydrocarbons; the alcohol may be mixed also with an active solvent selected from pyridine, quinoline or any other aliphatic, heterocyclic or aromatic base.

A further object of the present invention concerns the products obtained by means of the aforesaid process.

If inert solvents are employed, they consist of dinuclear compounds having the formula:

$$[Co''' (L_1 L_2 L_3 L_4)]_2 CR_1 R_2 O \cdot 2B$$

in which $R_1$ and $R_2$ are hydrogen, substituted and unsubstituted alkyl or aryl radicals, B is an alcohol, an ether, or the water itself if the reaction itself is carried out in presence of a water-alcohol mixture.

On the contrary, if active solvents are employed, the reaction products are mononuclear compounds having the formula $$[Co''' (L_1 L_2 L_3 L_4)] CR_1 R_2 R_3 O \cdot CR_1 R_2 R_2 OH \cdot B$$

in which $R_1$, $R_2$ and $R_3$ are hydrogen, an alkyl or an aryl radical, and B is selected from the above mentioned bases.

Moreover, it has been found, that is the thid object of the present invention, the above oxidation products can react with compounds having the formula $$HA - X$$

wherein A is a divalent radical selected from the following ones

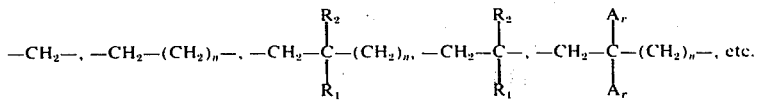

or a substituted radical as

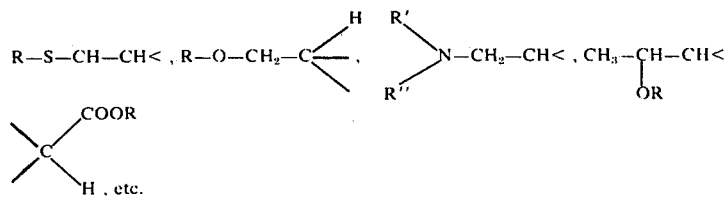

and X is a functional group as $-NO_2$, $-CN$, $CH_3CO-$, $-CHO$, etc.; this reaction produces trivalent cobalt derivatives, which are the fourth object of the present invention and have the general formula:

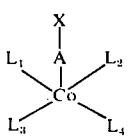

wherein A and X have the above reported meanings.

Typical unrestrictive examples of the insertion process according to the present invention, are the reactions with acetone, nitromethane, acetonitrile, acetaldehyde which form the following products

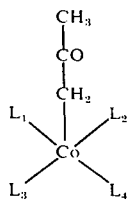
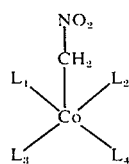

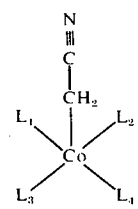
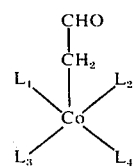

The insertion process according to the present invention can be carried out by suspending or dissolving the starting trivalent cobalt compounds either into the corresponding pure reactant or into the reactant diluted by the alcohol itself or by inert solvents. If the A radical of the HAX reactant is among those of the second group, the above process may be carried out by starting both from the β-substituted compound and from the corresponding unsaturated compound in presence of the mercaptan, the alcohol, the amine derivative and so on.

Crystalline derivatives are obtained with quantitative yields with respect both to the feed reactants and to the reaction products, which may be the final complexes and the oxidized alcoholic residues of the starting compounds.

The reactions may be carried out at a temperature ranging from 0° to 80° C, a slight heating being however preferable in order to increase the reaction rate.

The products which are the object of the present invention, may be employed as catalysts, in the dye industry, as intermediates in the dimerization reactions of monofunctional molecules in order to obtain double chain and difunctional molecules as it is described in a copending patent application of the same applicant.

The invention will now be illustrated by the following examples which have not to be understood as restrictive of it.

EXAMPLE I g. 4 of Co (II) Salen [bis-(salicylaldehyde)-ethylenediiminate] were suspended into 50cc of methyl alcohol at room temperature. Oxygen was allowed to bubble into the suspension for about 3 hours under stirring.

The solid compound, obtained at the end of the reaction was filtered and washed by ether, and then dried under vacuum. The yield was higher than 90%.

EXAMPLES 2–4

By working at the same conditions of the preceding example g. 4 of Co-Salen were suspended into ethylene chlorohydrin, benzyl alcohol and allyl alcohol.

The obtained solid compound was filtered, washed by ether and then dried under vacuum. The yields were higher than 90%.

EXAMPLE 5 g. 4 of Co-Salen were suspended into methyl alcohol containing about 10% of pyridine, at room temperature.

Oxygen was allowed to bubble for about 3 hours under stirring. The crystals of the trivalent cobalt pyridinate compound were isolated at the end of the reaction. The yield was quantitative.

EXAMPLE 6 g. 4 of Co-Salen, oxidized in methyl alcohol, were suspended into a mixture consisting of 25 cc of nitromethane and 25 cc of methyl alcohol.

The suspension was heated for some minutes at 50°–60° C and then cooled at room temperature.

The solid compound was filtered, washed by ether and dried under vacuum.

A higher than 80% yield was obtained.

EXAMPLES 7–9

By working at the same conditions of the preceding example, three suspensions of the cobalt complex oxidized in methyl alcohol were formed; the first suspension consisted of 4 g. of the cobalt complex in a mixture of methyl alcohol and acetone; the second was consisting of 4 g of the cobalt complex suspended into a methyl alcohol-acetonitrile mixture and the third suspension was obtained by 4 g. of the cobalt complex in a methyl alcohol-acetaldehyde. Crystalline solid compounds were always obtained at yields higher than 90%.

What we claim is:

1. A process for the preparation of tetradentate complexes of trivalent cobalt having the formula: $CO^{III}$ $(L_1L_2L_3L_4)$ $CR_1R_2O$. $CR_1R_2OH.B$ wherein $(L_1L_2L_3L_4)$ is a planar tetradentate ligand selected from bis-(diacetylmonooximenimino)-propane, bis-(salicylaldehyde)-ethylenediamine and bis-(acetylacetone)-ethylenediamine; $CR_1R_2O$ is an alcohol group selected from $CH_3O$, $CL\ CH_2\ CH_2O$, $OCH_2O$ and $CH_2\!-\!CH\!-\!CH_2O$; $CR_1R_2\ OH$ is the corresponding alcohol; and B is a heterocylic aromatic base selected from pyridine and quinoline which consists of reacting a mixture of cobalt complex $Co(L_1L_2L_3L_4)$, alcohol $CR_1R_2OH$ and heterocyclic amine base B with molecular oxygen at a temperature of from 0° to 70° C.

2. The process of claim 1 wherein $(L_1L_2L_3L_4)$ is bis-(salicylaldehyde)-ethylenediamine and B is pyridine.

3. The process of claim 1 wherein $(L_1L_2L_3L_4)$ is bis-(salicylaldehyde)-ethylenediamine and B is quinoline.

* * * * *